United States Patent
Barrett et al.

(10) Patent No.: US 10,729,625 B2
(45) Date of Patent: Aug. 4, 2020

(54) SELF ADAPTING POLYMERS FOR ANHYDROUS SUNSCREEN FORMULATIONS

(75) Inventors: Christine M. Barrett, Oakland, NJ (US); Hani M. Fares, Somerset, NJ (US); Rita Marie Guerrero, Hillsborough, NJ (US); Donald I. Prettypaul, Englewood, NJ (US); Tracey Ross, Hewitt, NJ (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 13/575,530

(22) PCT Filed: Feb. 4, 2011

(86) PCT No.: PCT/US2011/023701
§ 371 (c)(1),
(2), (4) Date: Oct. 5, 2012

(87) PCT Pub. No.: WO2011/097448
PCT Pub. Date: Aug. 11, 2011

(65) Prior Publication Data
US 2013/0243703 A1 Sep. 19, 2013

Related U.S. Application Data

(60) Provisional application No. 61/301,453, filed on Feb. 4, 2010, provisional application No. 61/301,469, filed on Feb. 4, 2010.

(51) Int. Cl.
*A61K 8/18* (2006.01)
*A61Q 17/04* (2006.01)
*A61K 8/35* (2006.01)
*A61K 8/81* (2006.01)

(52) U.S. Cl.
CPC .............. *A61K 8/18* (2013.01); *A61K 8/35* (2013.01); *A61K 8/8164* (2013.01); *A61K 8/8182* (2013.01); *A61Q 17/04* (2013.01); *A61K 2800/31* (2013.01); *A61K 2800/54* (2013.01)

(58) Field of Classification Search
CPC ......... A61K 8/8182; A61K 8/90; A61Q 17/04
See application file for complete search history.

(56) References Cited

U.S. PATENT DOCUMENTS

| | | | |
|---|---|---|---|
| 5,558,071 A * | 9/1996 | Ward | F02P 3/02 123/598 |
| 6,579,851 B2 * | 6/2003 | Goeke | A61K 38/26 514/11.7 |
| 8,461,129 B2 * | 6/2013 | Bolduc | A61L 15/28 127/49 |
| 2003/0124070 A1 | 7/2003 | Gonzalez et al. | |
| 2005/0186159 A1 * | 8/2005 | Gonzalez | A61K 8/35 424/59 |
| 2005/0192187 A1 | 9/2005 | Wagner et al. | |
| 2006/0008427 A1 | 1/2006 | Dueva et al. | |
| 2008/0050322 A1 | 2/2008 | Bandyopadhyay et al. | |
| 2008/0181858 A1 * | 7/2008 | Davis | A61K 8/73 424/59 |
| 2009/0035234 A1 * | 2/2009 | Cunningham | A61K 8/046 424/59 |
| 2010/0272657 A1 * | 10/2010 | He | A61K 8/046 424/59 |
| 2011/0028412 A1 * | 2/2011 | Cappello | A61K 31/7004 514/25 |
| 2013/0041004 A1 * | 2/2013 | Drager | A61K 9/08 514/394 |
| 2013/0084243 A1 * | 4/2013 | Goetsch | C07K 16/2863 424/1.49 |
| 2013/0096073 A1 * | 4/2013 | Sidelman | A61K 38/1709 514/21.6 |

OTHER PUBLICATIONS

Davis, J.A. et al. "Use of Film-Forming Polymer for Increased Efficacy in Sunscreens" J. Cosm. Sci. 2007 Annual Scientific Seminar, pp. 568-569.*
Ellis, L.N. et al. "A Simple Extraction Experiment" J. Chem. Educ., 1960, 37 (10), p. 510.*
Davis, J.A. et al. "Use of Film-Forming Polymers for Increased Efficacy in Sunscreens" J. Cosm. Sci. 2007 Annual Scientific Seminar, 568-569 (Year: 2007).*
PCT International Search Report PCT/US2011/023701, dated Aug. 11, 2011, ISP Investments Inc.

* cited by examiner

*Primary Examiner* — Andrew S Rosenthal
(74) *Attorney, Agent, or Firm* — William J. Davis; Nathalie Tietcheu

(57) ABSTRACT

Compositions comprising sun-care actives and self adapting polymers are disclosed. Self adapting polymers align themselves with the hydrophilic group pointing to the surface during application thus delivering an aesthetically pleasing surface to the consumers with a pleasant after feel. These polymers then rearrange upon contact with water so that the hydrophobic groups now point to the surface which then increases the water resistance of the formulation.

9 Claims, 1 Drawing Sheet

SELF ADAPTING POLYMERS FOR ANHYDROUS SUNSCREEN FORMULATIONS

CROSS REFERENCE TO RELATED APPLICATIONS

This application claims the benefit of U.S. Provisional Application Ser. No. 61/301,469 filed Feb. 4, 2010, and U.S. Provisional Application Ser. No. 61/301,453 filed Feb. 4, 2010, the entire contents of these documents are hereby incorporated by reference.

FIELD

The present application describes self adapting polymers and sunscreen compositions comprising self adapting polymers that become more hydrophobic when contacting water. The present application is also directed to SPF products exhibiting increased SPF values and more particularly to SPF formulations containing a polymer that boosts SPF in the composition. In accordance with one aspect, the composition may be a topically applied product on hair or skin that protects against UV damage. The product may contain one or more sunscreen agents and the polymer described herein at a level sufficient to boost SPF level.

BACKGROUND

Sunscreen compositions are typically used in sunny places. Consumers wearing sunscreen products are typically engaging in outdoor activities such as running and swimming. This makes sunscreen products constantly in contact with water and/or sweat. A key parameter in the development of anhydrous sprayable sunscreen is the ability to make such products hydrophobic so that their residence on skin is extended. Another key parameter relates to the development of sunscreen formulations having increased sun protection factor (SPF) values.

Non-aqueous sunscreen sprays have been increasing in popularity in the U.S. over the last few years. The composition of these sunscreen products is essentially based on the concept of dissolving the active ingredients (Sunscreens) in alcohol and adding a hydrophobic polymer to the products to make them water resistant. Additives such as boosters, preservatives, emollients, fragrance and skin conditioning agents may be added to such formulations. The addition of hydrophobic polymers to the skin may not be very pleasing to wear on the skin all day. Especially upon re-application, several coats of the hydrophobic polymer will accumulate and might be more uncomfortable to wear.

Hydrophobic polymers typically have been used to impart water proofing onto formulations. The hydrophobic polymers do not change their conformation upon exposure to water but stay unchanged as depicted in FIG. 1.

Higher SPF products are desirable to provide higher UV protection. One way of achieving higher SPF values is to increase the amount of sunscreens in the product. However, this approach will increase the cost of the product and might negatively impact the sensory characteristics of the product. Currently, the main pathway to achieving high SPF values is to increase the UV absorbers to maximum allowable concentrations. Small amounts of UV absorbers, like butyl octyl salicylate, have also been added as boosters to formulations. SPF has also been increased by adding light scattering/refracting polymers to the product such as styrene/acrylates copolymers. In addition, in some instances, certain polymers like Tricontanyl PVP have been used to increase the SPF of the formulation (see U.S. Pat. No. 6,436,376).

A few film formers have the ability to boost the SPF of a formulation. The mechanism is generally attributed to the ability of the polymer to make a uniform film of the product onto the skin. The distribution of the sunscreen actives in the film is considered key to the boosting effect of such polymer. In addition, the uniformity of the film is also of great importance. Since the surface of the skin is really not very uniform, many polymers do not have the ability of forming continuous films on the skin. That is why not all film formers are considered SPF boosters. The ability to identify such classes of polymers is key to achieve higher SPF values with less sunscreen in the formulations.

SUMMARY

The present application describes sunscreen compositions comprising self adapting polymers. Self adapting polymers align themselves with the hydrophilic group pointing to the surface during application thus delivering an aesthetically pleasing surface to the consumers with a pleasant after feel. These polymers then rearrange upon contact with water so that the hydrophobic groups now point to the surface which then increases the water resistance of the sunscreen formulation.

The present application is also directed to compositions containing a polymer that helps boost SPF in various formulations. In accordance with one aspect, the polymer contains at least one vinyl acetate and acrylate moiety.

The present application also provides a method for enhancing the SPF-value of one or more sun-care actives in UV-photoprotecting sun-care compositions comprising admixing and intimately formulating a pharmaceutically/cosmetically/dermatologically acceptable carrier and a copolymer or terpolymer as described herein in an amount effective to enhance the SPF value of the one or more sun-care actives.

DETAILED DESCRIPTION

Figure 1:
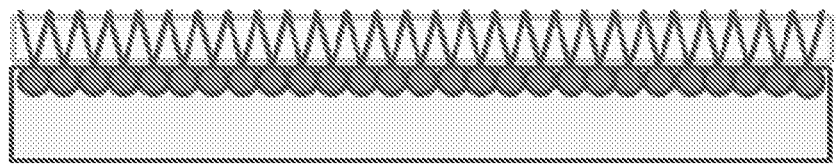
FIG. 1 is a partial, schematic view illustrating a hydrophobic film on a substrate.
Figure 2:
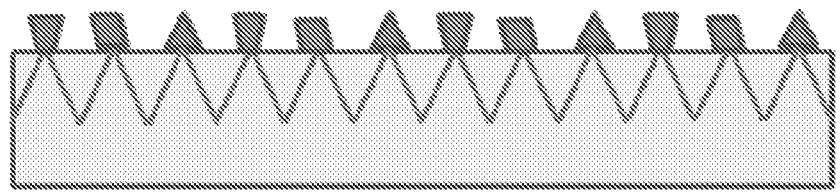
FIGS. 2 and 3 are partial, schematic views illustrating the alignment of self adapting polymers before and after contact with water, respectively.
Figure 3:
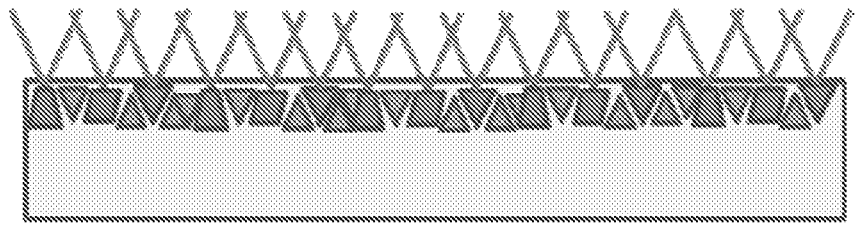

The present application is directed to self adapting polymers, and, more particularly, to self adapting polymers for use in anhydrous sunscreen formulations. In accordance with another aspect, the present application is also directed to sunscreen compositions or other compositions requiring a certain SPF value wherein the composition contains a polymer that boosts the SPF of the composition.

Sunscreen compositions disclosed herein contain a relatively hydrophilic polymer that will become hydrophobic upon exposure to water and/or sweat thus making the composition water resistant. Since the self-adapting polymer becomes hydrophobic when in contact with water, the products developed with such polymers can be used at home and in the same time at the beach or during activities.

It is very difficult to predict this behavior based on the structure of the polymer alone. Several factors may contribute to the ability of the polymer to behave in this manner. Some of these factors are listed below:
1. Molecular weight of the polymer
2. Monomer composition and type of such polymer
3. Monomer distribution throughout the polymer
4. Solubility of the polymer in the sunscreen formulation used and its residual phase.
5. Charge density of the polymer These parameters contribute to the behavior of the polymer and may dictate the change in conformation of such polymer from a hydrophilic one to a more hydrophobic one. This is illustrated in the example below. The same polymer was used in the two formulations. In one, the polymer was neutralized with aminoethyl propanol and in the other it was not neutralized. In the first case, the formula became more hydrophobic upon immersion in water whereas, in the second case the formulation became more hydrophilic.

TABLE 1

| INCI NAME | TRADE NAME | Formulations | |
|---|---|---|---|
| | | 11916-48-1 | 11916-26-1 |
| Avobenzone | Escalol 517 | 3.00 | 3.00 |
| Oxybenzone | Escalol 567 | 6.00 | 6.00 |
| Homosalate | | 15.00 | 15.00 |
| Octisalate | Escalol 587 | 5.00 | 5.00 |
| Octocrylene | Escalol 597 | 10.00 | 10.00 |
| Ethanol | | 60.49 | 60.50 |
| VP/Acrylates/Laurylmethacrylate Copolymer | Styleeze ® 2000 | 0.50 | 0.5 |
| Aminomethyl Propanol | AMP 95 | 0.01 | 0.0 |
| Total | | 100.00 | 100.00 |
| Contact Angle (°) Before Immersion | | 52.95 | 63.5 |
| Contact Angle (°) After Immersion | | 65.75 | 55.25 |

The sunscreen compositions described herein include a polymer additive that becomes more hydrophobic upon exposure to water. In accordance with certain aspects of the present invention, the conversion of a relatively hydrophilic polymer to a more hydrophobic one can be determined by measuring the contact angle of formulations containing the polymer. In accordance with certain aspects, the polymer additive is present in an amount sufficient to increase the contact angle of the formulation by at least 5 degrees, more particularly at least about 10 degrees after immersion in water. In accordance with some aspects of the present invention, the final contact angle of the formulation may be 60° or higher to impart water resistance to the formulation.

The polymer additive may be present in an amount sufficient to make the resulting composition more hydrophobic after immersion in water or contact with water. In accordance with certain aspects, the polymer additive may be present in an amount of about 0.1% to about 10%, more particularly from about 0.25% to about 5%, still more particularly from about 0.5% to about 1.5%, and in certain cases about 1% polymer by weight based on the total weight of the composition.

In accordance with a particularly useful aspect of the invention, the polymer additive may be a vinyl caprolactam/VP/dimethylaminoethyl methacrylate copolymer, a VP/vinylcaprolactam/DMAPA acrylates copolymer, a vinylcaprolactam/VP/dimethylaminoethyl methacrylate/octyl acrylamide copolymer, or a VA/butyl maleate/isobornyl acrylate copolymer. These polymers can be used without neutralization and still provide for a composition that becomes more hydrophobic upon exposure to water.

In accordance with other aspects, the polymer may be modified such that it provides the desired property of becoming more hydrophobic upon immersion in water. For example, Styleeze 2000 (VP/acrylates/laurylmethacrylate copolymer) when neutralized with aminoethyl propanol when included in a sunscreen formulation results in a formulation that becomes more hydrophobic upon immersion in water. Other polymer additives that can be useful herein can readily be identified by one of ordinary skill in the art utilizing the methods set forth in more detail below.

The sunscreen compositions described herein may be anhydrous compositions. The compositions typically include a single liquid phase that may also include dispersed particles. In accordance with certain embodiments, these formulations may have less than 10%, more particularly less than 5%, less than 2%, or less than 1%, by weight water. In certain cases, the formulations are free of water. Anhydrous solvents that may be used include, but are not limited to, alcohols such as ethanol, methanol, and isopropanol, volatile hydrocarbons such as isooctane, isododecane, and isohexadecane, aldehydes, volatile silicones, and volatile ketones such as acetone and MEK.

The sunscreen compositions of the invention can contain one or more sun-care actives. In particular, the compositions may contain active UVA and/or UVB sunscreen compounds, e.g., avobenzone, benzophenone-3, p-Aminobenzoic acid (PABA), Camphor benzalkonium methosulfate, Phenylbenzimidazole sulfonic acid, Terephthalidene dicamphor sulfonic acid, Benzylidene camphor sulfonic acid, Octocrylene, Polyacrylamidomethyl benzylidene camphor, Ethylhexyl methoxycinnamate, PEG-25 PABA, Isoamyl p-methoxycinnamate, Ethylhexyl triazone, Drometrizole trisiloxane, Diethylhexyl butamido triazone, 4-Methylbenzylidene camphor, 3-Benzylidene camphor, Ethylhexyl salicylate, Ethylhexyl dimethyl PABA, Benzophenone-4, Benzophenone-5, Methylene bis-benztriazolyl tetramethylbutylphenol, Disodium phenyl dibenzimidazole tetrasulfonate, Bis-ethylhexyloxyphenol methoxyphenol triazine, and Polysilicone-15. Other compounds described in the art for the purpose may also be used. The one or more sun-care actives can be used in an amount from about 1 wt. % to about 50 wt. % of the total weight of the composition.

The compositions may also contain one or more physical sun blockers. Examples of physical sun blockers include cerium oxides, chromium oxides, cobalt oxides, iron oxides, red petrolatum, silicone-treated titanium dioxides, titanium dioxides, zinc oxides, and/or zirconium oxides and mixtures thereof.

The sun-care composition of the present invention may provide an SPF value of at least 2, at least 4, at least 8, at least 10 or at least 15. More particularly, it may provide an SPF of at least 25 and in another particular embodiment of the invention provides an SPF of from about 50 to about 130.

In accordance with certain aspects of the present invention, the compositions described herein may exhibit a percent increase in boost (as described in more detail below) of at least 50%, more particularly at least 60%, and in accordance with certain embodiments at least 70% as compared to control compositions that do not contain the polymer additive. Of course, the compositions set forth herein may be advantageous even when exhibiting boosts as low as 5%, 10%, 20%, 25%, 30% or 40%. SPF boost values can be determined using the calculations set forth in the Food and Drug Administration (FDA) proposed amendments of the Final Monograph on Sunscreen Products for Over-the- Counter Human Use as published in the Federal Register on Aug. 27, 2007 at Volume 72, Number 165, pages 49070-49122, the contents of which are hereby incorporated by reference.

The compositions described herein can contain any of those compounds typically utilized in formulating sunscreen or other SPF compositions. More particularly, the sun-care composition of the present invention can further comprise one or more additional components selected from the group consisting of skin-feel additives, moisturizing agents, film former/waterproofing agents, pH adjuster/chelating agents, emulsifiers, preservatives, anti-aging agents, skin whitening agents, exfoliating agents, treatment ingredients, fragrances and mixtures thereof. Examples of other components that can be utilized in these compositions are described in U.S. Pat. No. 6,436,376, the contents of which are hereby incorporated by reference.

The sunscreen compositions may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention typically are then packaged in any package or container suitable for a sunscreen composition.

The compositions disclosed herein may be applied to the skin as a liquid rub on or as a spray. The compositions are not limited to those used primarily as sunscreens. The compositions may also be useful in other topically applied compositions where in the sunscreen active is a secondary ingredient in the formulation. Such formulations include lipsticks, make-up, lip balm, eye-shadow, hair dyes and conditioners or any application where sun protection may be deemed beneficial.

Figure 4:
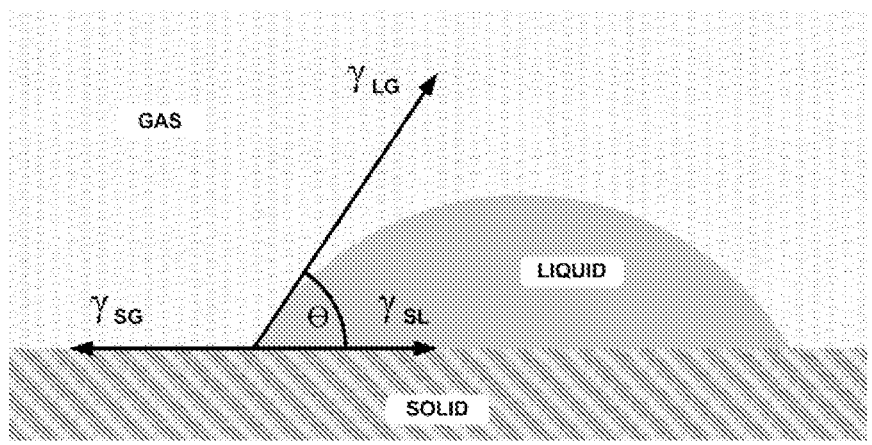
FIG. 4 is a schematic representation of the contact angle of a liquid droplet on a solid surface.

Contact angle is a measure of the ability of a liquid to wet a solid surface. FIG. 4 represents a schematic representation of a contact angle of a liquid droplet over a solid surface at the air solid-liquid contact point. The contact angle θ is the angle at which a liquid/vapor interface meets the solid surface. In general, molecules with a contact angle θ>90° do not wet a surface, whereas molecules with contact angle θ<90° wet a surface. It is generally accepted that the smaller the contact angles of a molecule, the better its wetting properties. The contact angle is specific for any given system and is determined by the interactions across the three interfaces, LV, SV, and SL. The subscripts S, L, and V, stand for solid, liquid, and vapor, respectively. Most often the concept is illustrated with a small liquid droplet resting on a flat horizontal solid surface using a goniometer. The contact angle is controlled by three forces: γSL (liquid vapor surface tension), γSV (solid vapor surface tension), and γSL (solid-liquid interfacial tension). A balance of the three relation leads to Young's equation:

$$\gamma SV = \gamma SL + \gamma LV \cos \theta$$

Contact angles of water droplets formed on sunscreen films deposited on PMMA (Polymethylmethacrylate) plates with an average surface roughness of 6 μm can be measured to identify useful polymers. Anhydrous sunscreen formulations with and without polymers were applied on polymethyl methacrylate (PMMA) plates. 1.2 mg/cm$^2$ of each formulation was applied on a 5×5 cm PMMA plate and was spread by hand using a finger cot. The measurements were conducted at 21-23° C. and a relative humidity (RH) of 24-35%. The static contact angle was measured, which means the drop is produced before the measurement and has a constant volume (5±2 μl) during the measurement. Readings were taken automatically every 5 seconds. Reported contact angles values represent an average of 10 trials (5 trials on two different silicone sheets). Images of the spreading droplet may be captured with a high-speed digital camera and analyzed by computer. An automated system marketed by the Krüss Company under the name of Drop Shape Analysis system (DSA 10) was used to determine the surface tension and contact angle measurements reported herein.

The invention will now be described in more detail by reference to the following non-limiting examples. Unless noted otherwise, the reported values indicate the percent by weight of the composition.

TABLE 2

| | | Formulations Tested | | | |
|---|---|---|---|---|---|
| INCI NAME | TRADE NAME | 11916-22-1 | 11916-23-1 | 11916-34-1 | 11916-35-1 |
| Avobenzone | Escalol 517 | 3.00 | 3.00 | 3.00 | 3.00 |
| Oxybenzone | Escalol 567 | 6.00 | 6.00 | 6.00 | 6.00 |
| Homosalate | | 15.00 | 15.00 | 15.00 | 15.00 |
| Octisalate | Escalol 587 | 5.00 | 5.00 | 5.00 | 5.00 |
| Octocrylene | Escalol 597 | 10.00 | 10.00 | 10.00 | 10.00 |
| Ethanol | | 58.00 | 58.00 | 60.00 | 60.00 |
| Vinylcaprolactam/VP/Dimethylaminoethyl Methacrylate Copolymer | Advantage ® S | 1.50 | 0.5 | | |
| VP/Vinylcaprolactam/DMAPA Acrylates Copolymer | Aquaflex ® SF 40 | 1.50 | 2.5 | | |
| Vinylcaprolactam/VP/Dimethylaminoethyl Methacrylate Copolymer | | | | 1.00 | |
| Vinylcaprolactam/VP/Dimethylaminoethyl Methacrylate/Octyl Acrylamide Copolymer | | | | | 1.00 |
| Total | | 100.00 | 100.00 | 100.00 | 100.00 |
| Contact Angle (°) Before Immersion | | 46.63 | 48.13 | 48 | 21 |
| Contact Angle (°) After Immersion | | 62.13 | 64.1 | 62.90 | 60.90 |

TABLE 3

| INCI NAME | TRADE NAME | Formulations Tested | |
|---|---|---|---|
| | | 11916-44-1 | 11925-95-1 |
| Avobenzone | | 3.00 | 3.00 |
| Oxybenzone | | 6.00 | 5.00 |
| Homosalate | | 15.00 | 10.00 |
| Octisalate | | 5.00 | 5.00 |
| Octinoxate | | | |
| Octocrylene | | 10.00 | 10.00 |
| Ethanol | | 59.00 | 65.00 |
| VA/Butyl Maleate/Isobornyl Acrylate Copolymer | Advantage ® Plus | 2.00 | 2.00 |
| Total | | 100.00 | 100.00 |
| Contact Angle (°) Before Immersion | | 58.70 | 63.05 |
| Contact Angle (°) After Immersion | | 69.35 | 69.35 |

SPF Boost Examples:

Formulations made with and without boosting polymers were prepared. These formulations are displayed below. The absorbances of these formulations were measured in vitro according to the following protocol:
1. A standard amount (0.8 mg/cm2) of formulation was applied onto a PMMA plate and spread evenly to obtain a uniform film.
2. The plates were left to equilibrate for about 15 minutes before any measurements were taken
3. The plates were measured in a UV spectrophotometer (Varian 300 UV-VIS) equipped with a labsphere (DRA-CA-30I).
4. Transmittance spectra were generated and converted to absorbance spectra.
5. An increase in the in vitro absorbance typically relates to an increase in sun protection which is translated to an increase in SPF value.

TABLE 4

| INCI Name | Control I | | | Control II | | |
|---|---|---|---|---|---|---|
| | 11925-52-14 | 11925-95-1 | 11925-95-2 | 11925-48-7 | 11925-136-1 | 11925-131-1 |
| Avobenzone | 3.00 | 3.00 | 3.00 | 3.00 | 3.00 | 3.00 |
| Homosalate | 10.00 | 10.00 | 10.00 | 15.00 | 15.00 | 15.00 |
| Octisalate | 5.00 | 5.00 | 5.00 | 5.00 | 5.00 | 5.00 |
| Benzophenone-3 | 5.00 | 5.00 | 5.00 | 6.00 | 6.00 | 6.00 |
| Octocrylene | 10.00 | 10.00 | 10.00 | 10.00 | 10.00 | 10.0 |
| VA/Butyl Maleate/Isobornyl Acrylate Copolymer (Advantage Plus) | 0 | 2.00 | 3.00 | | 2.00 | 3.00 |
| Ethanol | QS | QS | QS | QS | QS | QS |
| Percent Boost | N/A | 66% | 79% | N/A | 69% | 73% |

What is claimed is:

1. An anhydrous sprayable composition consisting of a sun-care active, a self-adapting polymer which aligns with a hydrophilic group pointing to the surface during application to a surface, and anhydrous ethanol,
    wherein the self-adapting polymer is Vinylcaprolactam (Vcap)/Vinylpyrrolidone (VP)/Dimethylaminoethyl methacrylate copolymer and is present in 0.05 wt. % to 10 wt. % of the total weight of the composition,
    the sun-care active consists of (i) avobenzone and (ii) at least one additional sun-care active selected from the group consisting of benzophenone-3, p-aminobenzoic acid (PABA), camphor benzalkonium methosulfate, phenylbenzimidazole sulfonic acid, terephthalidene dicamphor sulfonic acid, benzylidene camphor sulfonic acid, octocrylene, polyacrylamidomethyl benzylidene camphor, ethylhexyl methoxycinnamate, PEG-25 PABA, isoamyl p-methoxycinnamate, ethylhexyl triazone, drometrizole trisiloxane, diethylhexyl butamido triazone, 4-methylbenzylidene camphor, 3-benzylidene camphor, ethylhexyl salicylate, ethylhexyl dimethyl PABA, benzophenone-4, benzophenone-5, methylene bis-benztriazolyl tetramethylbutylphenol, disodium phenyl dibenzimidazole tetrasulfonate, bis-ethylhexyloxyphenol methoxyphenol triazine, polysilicone-15, and combinations thereof,
    the composition does not contain a neutralizer,
    the composition is a homogeneous single-phase and exhibits an increase in hydrophobicity after contact with water,
    the composition exhibits a percent increase in SPF (sun protection factor) boost of at least 50% as compared to control compositions that do not contain the polymer, and
    wherein the anhydrous ethanol is present in 59.0 wt. % to 65.0 wt. % of the total weight of the composition.

2. The composition according to claim 1, having an SPF of at least 10.

3. The composition according to claim 1, wherein the one or more sun-care actives are present in an amount of 1 wt. % to 50 wt. % of the total weight of the composition.

4. The composition according to claim 1, wherein the self adapting polymer comprises 0.25% wt. % to 5 wt % of the total weight of the composition.

5. The composition according to claim 4, wherein the self adapting polymer comprises 0.5 wt. % to 2 wt. % of the total weight of the composition.

6. The composition according to claim 1, wherein the composition exhibits an increase in contact angle of at least 5° after immersion in water.

7. The composition according to claim 1, further comprising one or more additional components selected from the group consisting of skin-feel additives, moisturizing agents film former/waterproofing agents, pH adjuster/chelating agents, emulsifiers, preservatives, and mixtures thereof.

8. The composition according to claim 1, wherein the composition does not contain an amine neutralizer.

9. The composition according to claim 1, wherein the Vinylcaprolactam(Vcap)/Vinylpyrrolidone (VP)/Dimethylaminoethyl methacrylate copolymer is present in 2 wt. % to 3 wt. % of the total weight of the composition and wherein the avobenzone is present in 3 wt. % of the total weight of the composition.

* * * * *